United States Patent [19]
Tabata

[11] Patent Number: 5,995,219
[45] Date of Patent: Nov. 30, 1999

[54] PATTERN DEFECT INSPECTION APPARATUS

[75] Inventor: Mitsuo Tabata, Yokohama, Japan

[73] Assignee: Kabushiki Kaisha Toshiba, Kawasaki, Japan

[21] Appl. No.: 09/035,268

[22] Filed: Mar. 5, 1998

[30] Foreign Application Priority Data

Mar. 5, 1997 [JP] Japan .................................. 9-050321

[51] Int. Cl.⁶ .................................................. G01N 21/88
[52] U.S. Cl. ....................................................... 356/237.5
[58] Field of Search ................................ 356/394, 237.5, 356/239.3; 382/144

[56] References Cited

U.S. PATENT DOCUMENTS 5,410,400 4/1995 Shishido et al. ...................... 356/237.4
5,814,829 9/1998 Broude et al. ...................... 250/559.46

FOREIGN PATENT DOCUMENTS

58-223328 12/1983 Japan .
59-192944 11/1984 Japan .
8-068618 3/1996 Japan .

*Primary Examiner*—Richard A. Rosenberger
*Attorney, Agent, or Firm*—Oblon, Spivak, McClelland, Maier & Neustadt, P.C.

[57] ABSTRACT

A pattern defect inspection apparatus. Light is irradiated on a sample having a pattern formed thereon and the transmitted or reflected portion of the irradiated light is condensed. The condensed light is received so as to acquire the observed data corresponding to the pattern formed in the sample. A design pattern image is compared with a pattern formed in the sample by the observed data. Alternatively, two sets of observed data corresponding to a plurality of patterns formed in the sample are compared. The presence or absence of a defect of the pattern is judged based on the result of comparison. This also determines whether the size of the defect of the pattern is larger than a predetermined size. The inspection is temporarily stopped if the size of the defect detected by the judging circuit during inspection is larger than a predetermined size.

12 Claims, 5 Drawing Sheets

PATTERN DEFECT INSPECTION APPARATUS

BACKGROUND OF THE INVENTION

The present invention relates to a pattern defect inspection apparatus, particularly, to an apparatus for inspecting defects of the photomask used in the manufacture of a semiconductor device and the pattern of the semiconductor wafer or for inspecting the defects of the pattern of a liquid crystal display substrate.

A defect of the photomask used in the manufacture of a semiconductor device by means of photolithography is one of the main reasons for the reduction in the yield of a large-scale integrated circuit (LSI). To overcome the difficulty, vigorous studies are being made in an attempt to develop an apparatus for inspecting the defect of the photomask.

The conventional mask defect inspection apparatus is roughly classified into a type in which two chips having the same pattern written therein are independently detected and observed, and the difference therebetween is compared by a suitable defect detecting means so as to detect the defect, and another type in which a pattern and a design data are compared by a defect detecting means so as to detect the defect. The former type is advantageous in that a design data is not required because the two chips having the same pattern written therein are separately observed and compared by different detecting means. However, the former type is unsatisfactory in that the same pattern is required to be formed in a plurality of regions of a single mask, with the result that a defect cannot be detected by comparison of the patterns formed in the mask. On the other hand, the latter type requires a design pattern used for comparison, leading to a complex circuit construction. However, since the defect is detected by comparison with the design pattern, a highly strict inspection can be achieved. In addition, the inspection can be performed even if only one pattern is formed in a single mask.

Where a defect has been found in the conventional inspection apparatus outlined above, the information such as the defective point and the coordinate position of the defective point are stored by some method, e.g., stored in a magnetic disk, and a review treatment is carried out after completion of the inspection over the entire region. The operator visually inspects the defective portion and judges whether a re-repair is required so as to transfer the inspected object to a repairing process, as required. Where repair is performed, the operator determines whether to perform a white defect repair for making up for a defective point or a black defect repair for deleting an extruding defect.

Figure 1A:
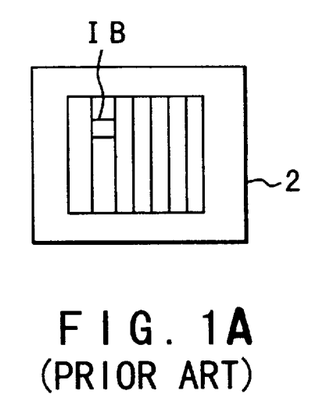
FIGS. 1A and 1B exemplify defects of a pattern.
Figure 1B:
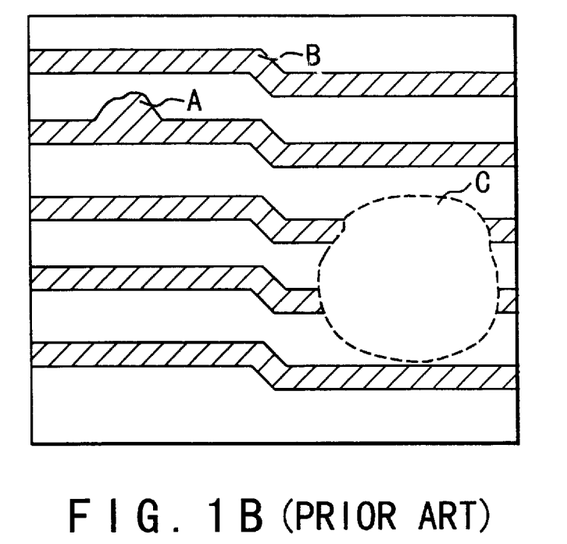

FIGS. 1A and 1B schematically exemplify a mask pattern and a defect thereof. A portion in a stripe of an inspection stripe shown in FIG. 1B is schematically shown in a magnified fashion in FIG. 1A. A shaded portion in FIG. 1A denotes a chromium portion (light shielding portion) of a mask 2, with a white portion representing a glass portion (transparent portion) of the mask 2. Portions A and B shown in the drawing denote defects of a standard size, e.g., about 0.2 to 2 $\mu$m, which can be repaired. Many of the defects are occupied by the defects of the standard size. On the other hand, it is difficult to repair portion C in which a large portion, e.g., on the order of 10 $\mu$m to 100 $\mu$m, of the chromium region is omitted. Such a large defect as cannot be repaired rarely takes place. However, the presence of such a large defect, even if only one defect is present, makes the mask quite unusable so as to be discarded.

In general, the mask is automatically inspected. After inspection on the entire region of a single mask, it is judged whether to repair the defect based on confirmation of the presence or absence of the defect and the type of the defect such as the lack of chromium, residue of chromium and dust (review treatment). A series of these operations take about one hour even where the operations are simple and 5 to 6 hours or more in some cases. Where such a large defect as not to be repaired is found unfortunately at the final stage of the operation, all the time spent up to then is rendered quite insignificant.

As described above, the review treatment is performed after inspection on the entire region of the mask in the conventional pattern defect inspection apparatus, with the result that it is impossible to know the presence of a large defect, which makes the mask unusable, until completion of the inspection over the entire region. In the manufacture of the up-to-date mask of this kind, it is important to shorten the turn-around time as much as possible. It should be noted that, if the presence of a large defect can be detected in an early stage, it is possible to take measures against the defect occurrence promptly or to make a quick decision to manufacture again the mask, with the result that the turn-around time can be shortened as a whole. Also, since an extra operation need not be carried out, the inspection system is enabled to perform its operation efficiently, leading to an improved productivity.

BRIEF SUMMARY OF THE INVENTION

An object of the present invention is to provide a pattern defect inspection apparatus capable of detecting a large defect in a relatively early stage so as to improve the efficiency of the inspection system.

According to a first aspect of the present invention, there is provided a pattern defect inspection apparatus, comprising: irradiating means for irradiating a light to a sample having a pattern formed therein; beam-condensing means for condensing the transmitted or reflected portion of the light irradiated to the sample by the irradiating means; observed data acquiring means for receiving the light condensed by the beam-condensing means so as to acquire the observed data corresponding to the pattern formed in the sample; comparing means for comparing a design pattern image data prepared on the basis of a design data corresponding to the pattern formed in the sample with the observed data or for comparing the observed data with another observed data corresponding to a plurality of patterns formed in the sample based on the same design data; judging means for judging the presence or absence of a defect of a pattern based on the result of comparison made by the comparing means and for also determining whether the size of the defect of the pattern is larger than the predetermined size; and stopping means for temporarily stopping the inspection where the size of the defect detected by the judging means during the inspection is judged to be larger than the predetermined size of a defect. Preferred manners of the pattern defect inspection apparatus are as follows.

(1) The observing means for observing the defect detected after the temporary stopping of the inspection performed by the stopping means, and instructing means for instructing an operation which is to be performed in the next step based on the result of the observation performed by the observing means are further provided.

(2) The instructing means gives instruction based on the result of observation made by the observing means as to whether to temporarily stop the inspection or to start up again the inspection.

(3) The judging means includes means for judging the type of the defect of the pattern based on the result of comparison made by the comparing means so as to set in advance the sizes of a plurality of defects conforming with the kinds of the defects.

(4) The predetermined sizes of the defects are judged on the basis as to whether the defect can be repaired or not.

(5) The judging means includes a first judging means for judging a first defect by differential comparison, and a second judging means for judging a second defect having a size larger than that of the first defect by means of level comparison.

According to a second aspect of the present invention, there is provided a pattern defect inspection apparatus, comprising: irradiating means for irradiating a light to a sample having a pattern formed therein; beam-condensing means for condensing the transmitted or reflected portion of the light irradiated to the sample by the irradiating means; observed data acquiring means for receiving the light condensed by the beam-condensing means so as to acquire the observed data corresponding to the pattern formed in the sample; comparing means for comparing a design pattern image data prepared on the basis of a design data corresponding to the pattern formed in the sample with the observed data or for comparing the observed data with another observed data corresponding to a plurality of patterns formed in the sample based on the same design data; first judging means for judging by a differential comparing method the presence or absence of a first defect of a pattern based on the result of comparison made by the comparing means; second judging means for judging the presence or absence of a second defect having a size larger than that of the first defect by means of a level comparing method; and stopping means for temporarily stopping the inspection where the second judging means has judged the presence of a second defect during the inspection.

(1) The observing means for observing the defect detected after the temporary stopping of the inspection performed by the stopping means, and instructing means for instructing the operation which is to be performed in the next step based on the result of the observation performed by the observing means are further provided.

(2) The instructing means gives instruction based on the result of observation made by the observing means as to whether to temporarily stop the inspection or to start up again the inspection.

(3) The second judging means includes means for judging the type of the defect of the pattern based on the result of comparison made by the comparing means so as to set a predetermined plurality of sizes of defects coinciding with the kinds of the defects.

(4) The sizes for judging the presence or absence of the second defect is judged on the basis as to whether the defect can be repaired.

According to the present invention, the inspection is temporarily stopped where the size of a pattern defect is judged to be larger than a predetermined size of the defect, making it possible to detect the presence of a large defect in a relatively early stage. As a result, the efficiency of the inspection system can be improved.

To be more specific, it is possible to know even during the inspection whether the detected defect is too large to be repaired. Where the defect has been found to be too large to be repaired, the inspection can be temporarily stopped instantly. In other words, the presence of such a decisive defect can be detected during the inspection, even if the entire region of the sample is not inspected. Also, where it is desired to know the type, shape, etc. of the defect, more detailed information on the defect can be obtained by visual observation by carrying out a review treatment after the temporary stopping of the inspection. Further, where a plurality of samples are inspected in succession, the waste time residing in general between inspection of the adjacent samples can be eliminated, if the inspection is set to be instantly finished, leading to an efficient inspection.

Further, even where the size of the defect is judged to be larger than that of the predetermined defect, it is possible for the defect to be confirmed by visual observation that the defect consists of a removable substance such as dust. In such a case, the sample is prevented from being discarded as being useless by giving an instruction to start up again the inspection once stopped temporarily.

According to the present invention, the inspection is temporarily stopped in the case where the size of the pattern defect is judged to be larger than that of the predetermined defect. It follows that it is possible to detect the presence of a large defect in a relatively early stage, leading to an improved efficiency of the inspection system.

It should also be noted that even where the size of the defect is judged to be larger than that of the predetermined defect, it is possible for the defect to be confirmed by visual observation that the defect consists of a removable substance such as dust. In such a case, the sample is prevented from being discarded as being useless by giving an instruction to start up again the inspection once stopped temporarily.

Additional objects and advantages of the present invention will be set forth in the description which follows, and in part will be obvious from the description, or may be learned by practice of the present invention. The objects and advantages of the present invention may be realized and obtained by means of the instrumentalities and combinations particularly pointed out in the appended claims.

BRIEF DESCRIPTION OF THE SEVERAL VIEWS OF THE DRAWINGS

The accompanying drawings, which are incorporated in and constitute a part of the specification, illustrate presently preferred embodiments of the present invention and, together with the general description given above and the detailed description of the preferred embodiments given below, serve to explain the principles of the present invention in which.

DETAILED DESCRIPTION OF THE INVENTION

Let us describe preferred embodiments of the present invention with reference to the accompanying drawings.

First, let us describe an example of a mask-reticle inspection apparatus described in, for example, ("High Precision Full Auto Mask-Reticle Inspection Apparatus for Ultra LSI", Electronics Material, September 1983, Page 47) for facilitating the understanding of the present invention.

Figure 2:
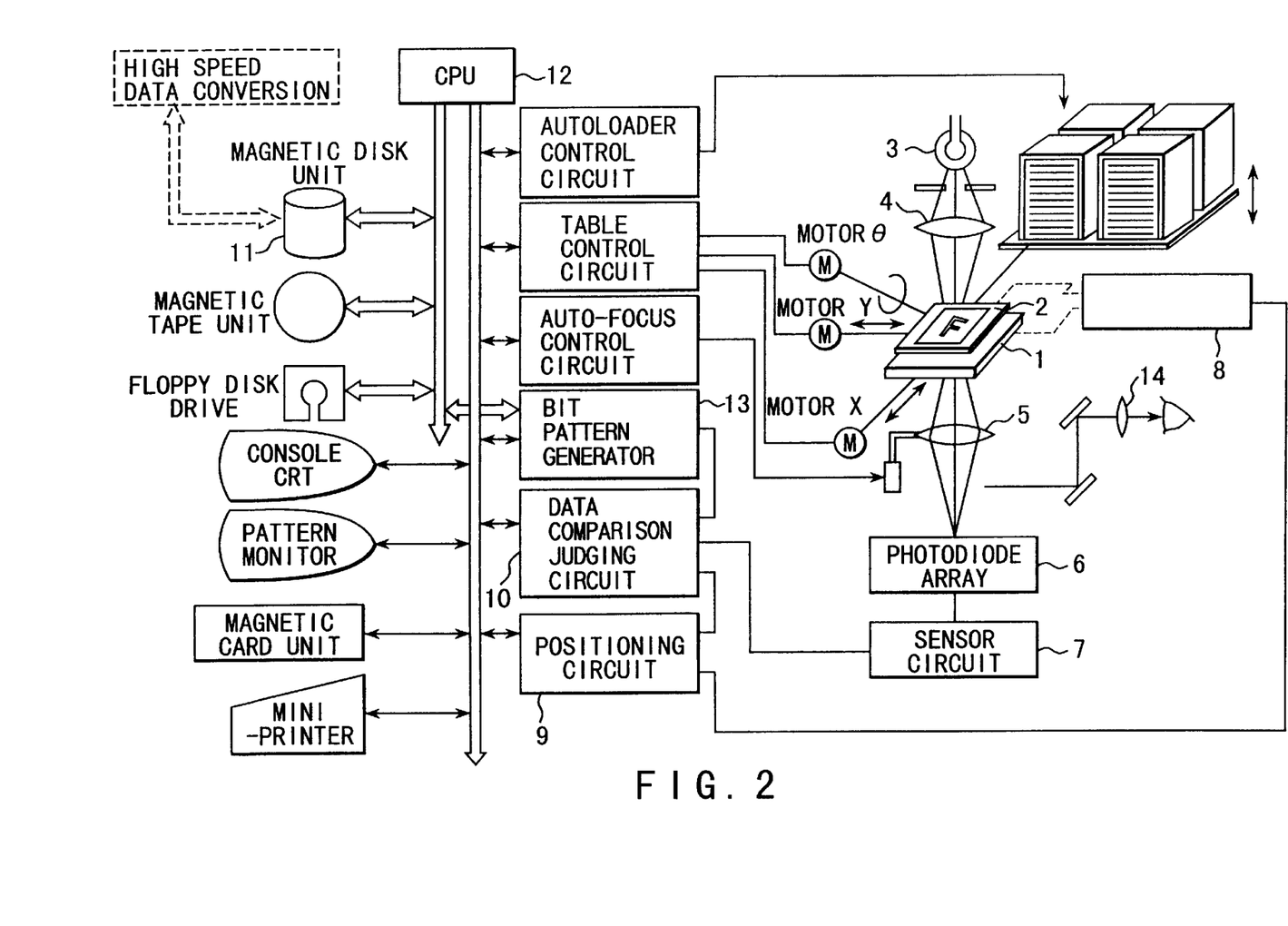
FIG. 2 shows the entire construction of a pattern defect inspection apparatus according to the present invention.
Figure 3A:
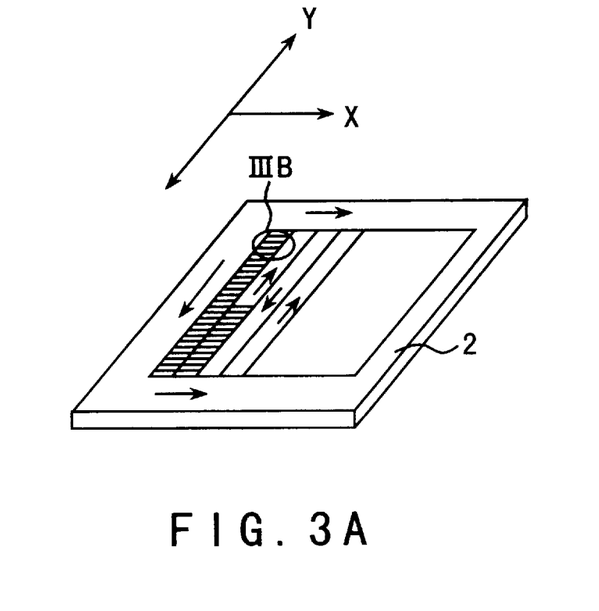
FIGS. 3A and 3B show the inspection unit, etc. within a sample in the case of performing a pattern defect inspection.
Figure 3B:
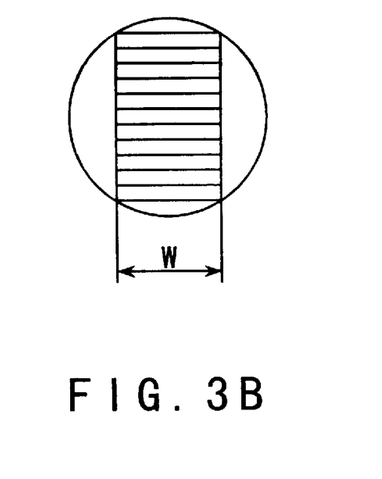

FIG. 2 shows the entire construction of the pattern defect inspection apparatus according to the present invention. FIGS. 3A and 3B show the inspection unit, etc. within a sample in the case of performing a pattern defect inspection.

An electron beam light-exposure apparatus is used for the manufacture of an ordinary mask, and the defect in the chromium portion of the mask is inspected by using the data equal to that used in the mask manufacture. In performing the inspection, the mask pattern written on a mask 2 is magnified with, for example, a microscope, and the inspection is performed by measuring continuously the slender striped portion having a width W of about 200 to 1,000 μm, as shown in FIGS. 3A and 3B, where a table is actually moved continuously.

First, the mask 2 is disposed on an XY θ-table 1, as shown in FIG. 2. Under this condition, a pattern written on the mask 2 is irradiated with light emitted from a light source 3 and transmitted through an optical system 4. The light transmitted through the mask 2 runs through an optical system 5 to reach a photodiode array 6 so as to form a pattern image on the photodiode array 6. An output corresponding to the pattern image imaged on the photodiode array 6 is sent to a sensor circuit 7 so as to be subjected to an A/D conversion. The observed data subjected to the A/D conversion in the sensor circuit 7 is sent to a comparing/judging circuit 10 together with a position data generated from a positioning circuit 9 based on the data generated from a laser length measuring system 8.

On the other hand, the design data corresponding to the pattern written on the mask 2 is forwarded from a magnetic disk apparatus 11 to a bit pattern generator 13 through a CPU 12 (control computer). A bit data is generated from the figure data within the bit pattern generator 13 and, then, the bit data is transferred into a comparing/judging circuit 10. A suitable filtering treatment is applied to the bit pattern data within the comparing/judging circuit 10 so as to provide a multi-valued equivalent. It should be noted that the observed data is obtained under the condition that a filtering function has been applied thereto because of the resolution characteristics of the optical system 5 and the aperture effect of the photodiode array 6. Therefore, an equivalent filtering treatment is applied to the bit pattern data obtained from the design data so as to allow the bit pattern data to coincide with the observed data. These data items thus obtained are compared with each other in accordance with a suitable algorithm, and a portion where these two data items do not coincide is judged to be a defect.

Where a defect is detected in an apparatus of this type, the defect information is stored in a memory with an inspection width W, which is about 200 to 1000 μm, used as a unit as shown in FIGS. 3A and 3B.

The present invention is featured mainly in the construction of the data comparing/judging circuit 10 shown in FIG. 2. Let us describe more in detail the construction of the data comparing/judging circuit 10 according to the first embodiment of the present invention with reference to FIG. 4.

Figure 4:
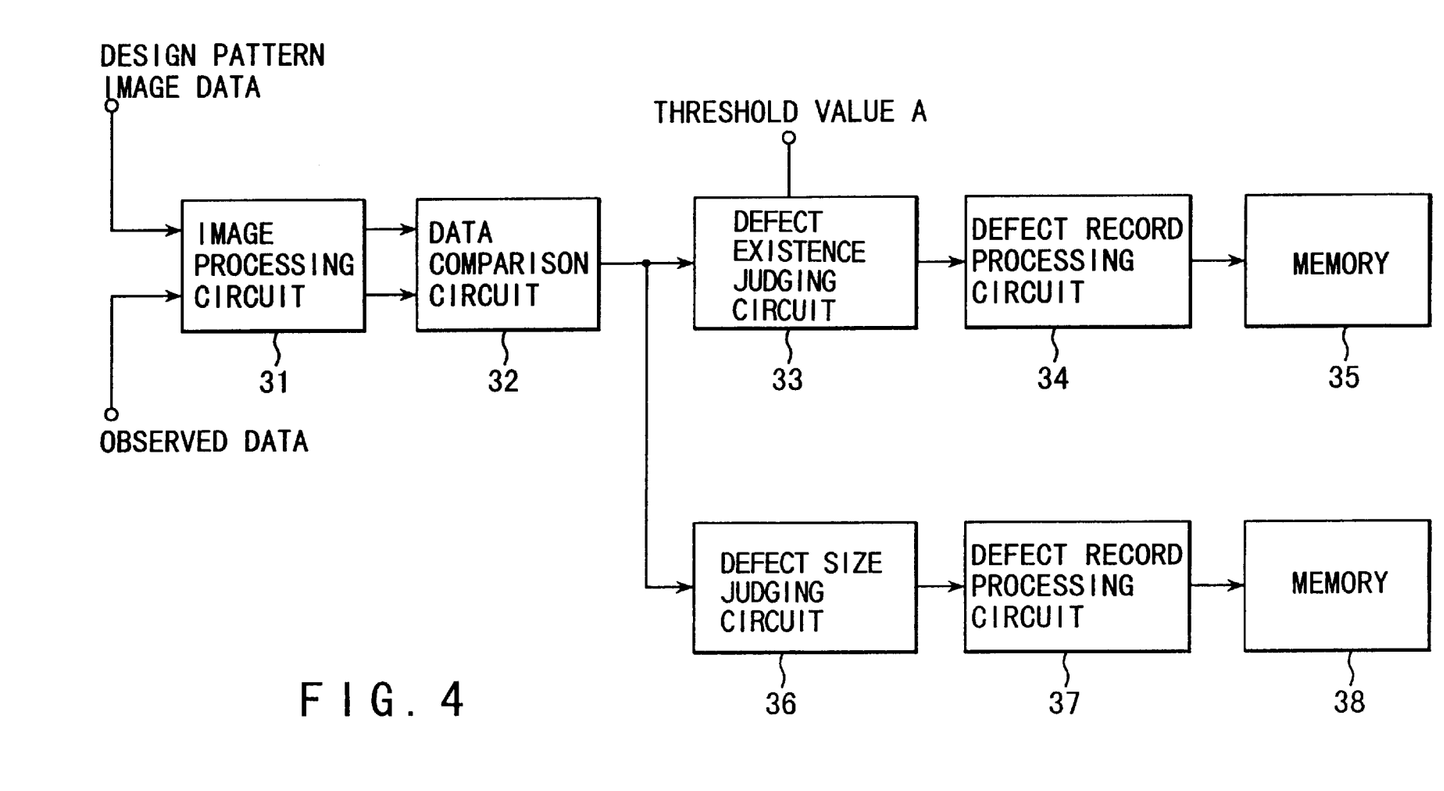
FIG. 4 is a block diagram showing the detailed construction of a comparing/judging circuit according to a first embodiment of the present invention.

As shown in the drawing, the observed data generated from the sensor circuit 7 shown in FIG. 2 and the design pattern image data generated from the bit pattern generator 13 shown in FIG. 2 are supplied to an image processing circuit 31 to produce two image data items. The two image data items produced in the image processing circuit 31 are compared within a data comparing circuit 32. To be more specific, after the two data items are subjected to an image processing within the image processing circuit 31 in accordance with a predetermined algorithm, these two data items are subjected to comparison treatment within the data comparing circuit 32 in accordance with a predetermined algorithm. The algorithms employed in the present invention include, for example, a system in which two data items are directly compared with each other and another system in which the gradients (differential values) relative to the positions are compared with each other. The algorithm employed in the present invention will be described herein later more in detail.

A defect existence judging circuit 33 is connected to the data comparing circuit 32. Where the output from the data comparing circuit 32 is greater than a predetermined threshold value A, the defect existence judging circuit 33 judges that there is a defect. A defect size judging circuit 36 is also connected to the data comparing circuit 32. Where the output from the data comparing circuit 32 is greater than a predetermined threshold value B, the defect size judging circuit 36 judges that there is a large defect. In short, the defect existence judging circuit 33 and the defect size judging circuit 36 differ from each other in the criterion (threshold value) based on which the existence of a defect is judged. The size of the defect is related to the threshold value for judging the presence of the defect. In general, the size of the defect to be detected is diminished with decrease in the threshold value. In the defect existence judging circuit 33, the threshold value A is set small so as to detect the defects of various sizes including large defects and small defects. On the other hand, the threshold value B is set large in the defect size judging circuit 36 so as to permit large defects alone to be detected. It should be noted, however, the magnitude of the threshold value B should be judged to permit the detected defects to be repaired.

A defect record processing circuit 34 is connected to the defect existence judging circuit 33. When a defect has been detected in the defect existence judging circuit 33, the defect record processing circuit 34 permits the information on the defect to be stored in a memory 35 connected to the circuit 34. On the other hand, a defect record processing circuit 37 is connected to the defect size judging circuit 36. When a large defect has been detected in the defect size judging circuit 36, the information on the large defect is stored in a memory 38 connected to the defect record processing circuit 37.

Incidentally, the construction shown in FIG. 4 excluding the defect size judging circuit 36, the defect record processing circuit 37 and the memory 38 is basically equal to the conventional construction disclosed in the literature quoted previously.

Figure 5:
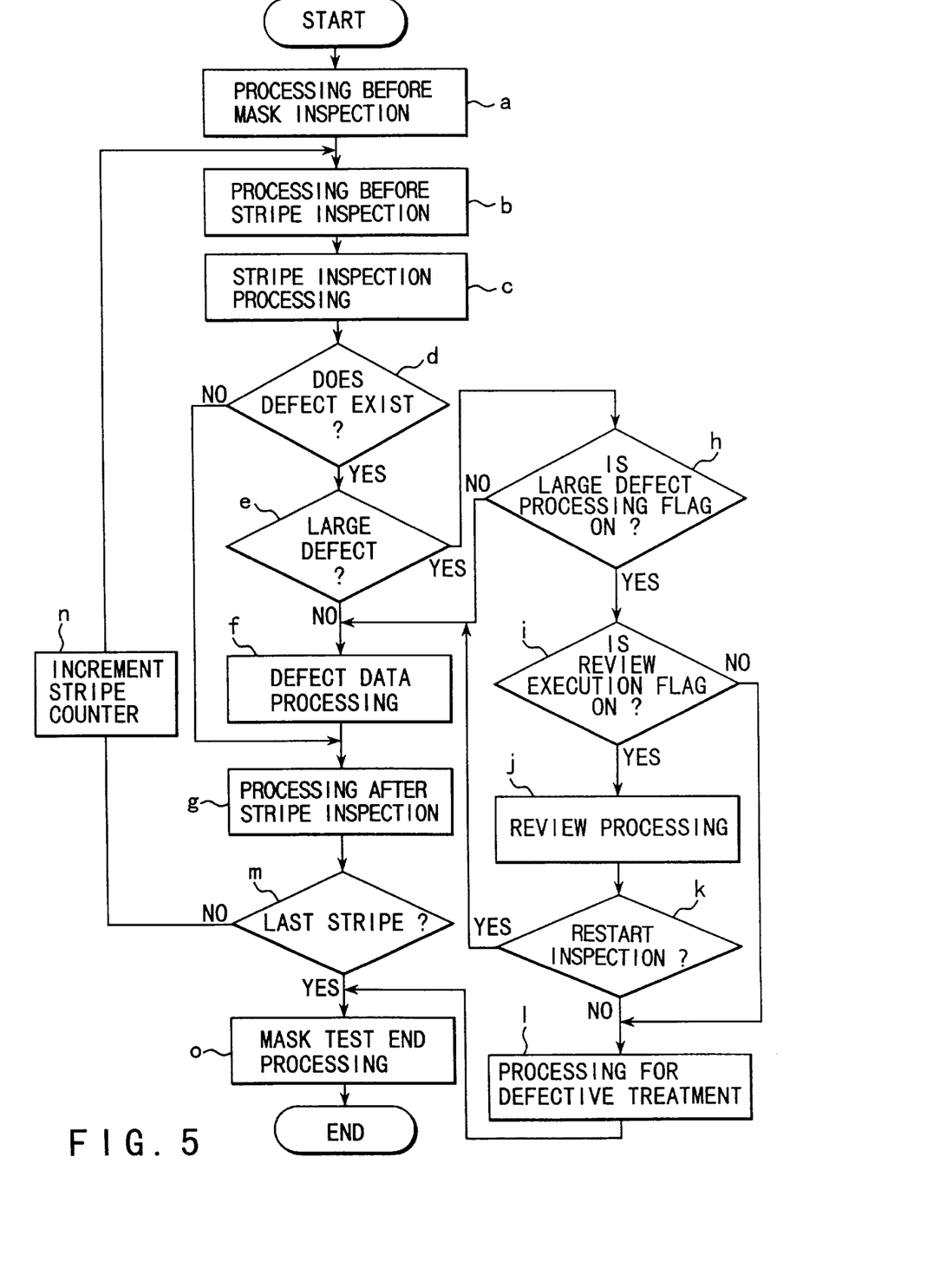
FIG. 5 is a flow chart exemplifying the flow of the inspection treatment performed by a pattern defect inspection apparatus according to the present invention.

FIG. 5 is a flow chart showing the flow of the specific inspections performed in the first embodiment of the present invention.

In the first step, a pretreatment for inspecting a single mask is performed (step a). The pretreatment for the mask inspection is a processing of information on, for example, the mask to be inspected, and includes, for example, a process for selecting the mask data used, a process for setting the conditions for the mask inspection, and an alignment process. In the alignment process, a deviation between an XY position within the mask plane when the mask is set and the rotation is read out so as to repair the deviation.

After the pretreatment for the mask inspection, the mask inspection treatments are carried out in steps b to m. In the mask inspection treatment, the inspection is performed with inspection region within the mask plane divided into fine strips each having an inspection width W (inspection stripe) as shown in FIGS. 3A and 3B. In this case, the data processing of the comparative inspection is carried out using each inspection stripe as a unit, and the inspection region is successively changed into the subsequent inspection stripe so as to perform inspection over the entire inspection region. To be more specific, the basic flow of the inspection includes a pretreatment for a stripe inspection (step b), a stripe inspection treatment (step c), and a post-treatment for the stripe inspection (step g) in respect of each inspection stripe as a unit.

After the stripe inspection treatment has been performed for a single inspection stripe in step c, the existence of a defect is judged by the defect existence judging circuit 33 (step d). Where a defect has been judged not to be present, the post-treatment for the stripe inspection is carried out (step g). Where a defect has been judged to be present, the size of the defect is judged in the defect size judging circuit 36 (step e). To be more specific, it is judged in the defect size judging circuit 36 whether the defect is sized larger than a predetermined size. Where the defect has been judged not to be a large defect, a defect data processing, in which the information on the defect such as the position of the defect is stored in a memory, is performed (step f), followed by performing the post-treatment for the stripe inspection (step g). Where the defect has been judged to be a large defect, a large defect processing is to be carried out.

In the large defect processing, it is judged whether a large defect processing flag is turned on (step h). The large defect processing flag is a flag judging whether or not large defect processing should be carried out, and is preset by the user before inspection. The larger defect processing flag is usually set at ON, but is set at OFF when the user does not want to carry out the large defect processing. The case is a case that the user wants to obtain distribution of occurrence of defects in entire region inspection even if inferior goods are produced, or the like. Where the large defect processing flag is not set at ON, that is, where the defect is not a decisive defect, a defect data processing is carried out (step f), followed by performing the post-treatment for the stripe inspection (step g). Where the large defect processing flag is set at ON, i.e., where the defect is a decisive defect, the inspection is temporarily stopped, followed by judging whether a review execution flag is turned on (step i). The review execution flag is a flag whether or not a review is carried out, and is preset at predetermined inspection conditions before inspection. The flag is usually set at ON, but is set at OFF when the user does not want to carry out the review treatment during inspection. This is in case a plurality of masks are successively inspected or the like. Where the review execution flag has been judged not to be set at ON, a processing for defective treatment is instantly carried out (step l) without performing the review processing, followed by performing a mask inspection end processing (step o). Where the review execution flag has been judged to be set at ON, a review processing is carried out (step j).

In the review processing, the operator observes the defect with an observing scope 14 shown in FIG. 2. Based on the result of the observation, the operator gives an instruction by a prejudged instructing means as to the processing which is to be performed in the next step. As described previously, the threshold value set for the defect size judging circuit 36 is judged on the basis of a criterion as to whether the defect is sized to be capable of repair. Therefore, the mask whose defect has been judged to be a large defect is discarded as an unsatisfactory article. However, even where the defect has been judged to be a large defect, it is possible for the defect to consist of, for example, a removable substance such as dust attached to the mask. In this case, the mask need not be discarded as an unsatisfactory article. In view of the particular situation, the operator gives an instruction as to whether the inspection which has been temporarily stopped is finished as it is or whether the inspection temporarily stopped is continued again. Where the inspection has been judged not to be started again but to be finished (step k), a processing for a defective treatment is performed (step l), followed by a mask inspection end processing (step o). On the other hand, where the inspection has been judged to be continued again (step k), a defect data processing is performed (step f), followed by performing a processing after stripe inspection (step g). In general, the operation proceeds to the next inspection for an inspection stripe.

A prejudged after-treatment is performed in the processing after the stripe inspection (step g), and it is judged whether the inspection stripe is the final inspection stripe (step m). Where the inspection stripe has been judged not to be the final inspection stripe, a stripe counter is counted up (step n), followed by inspecting on the next inspection stripe. On the other hand, where the inspection strip has been judged to be the final inspection stripe, a mask inspection end processing is carried out (step o) so as to finish the inspection over the entire mask region.

Figure 6:
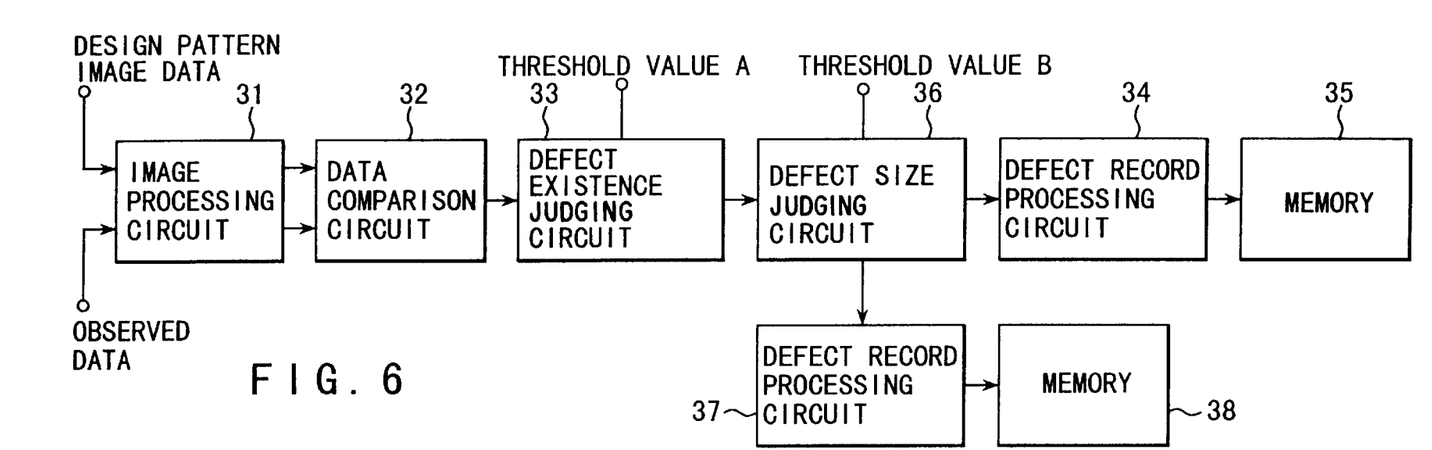
FIG. 6 is a block diagram showing the detailed construction of a comparing/judging circuit according to a second embodiment of the present invention.

FIG. 6 is a block diagram showing the construction in detail of the comparing/judging circuit according to a second embodiment of the present invention. The constituents of the circuit shown in FIG. 6, which are equal to those included in the circuit shown in FIG. 4, are denoted by the same reference numerals so as to omit the detailed description thereof.

In the first embodiment shown in FIG. 4, the output signal generated from the data comparing circuit 32 is supplied to both the defect existence judging circuit 33 and the defect size judging circuit 36 so as to judge the existence of the defect in parallel. In the second embodiment shown in FIG. 6, however, the existence of an ordinary defect is judged first in the defect existence judging circuit 33, followed by judging the existence of a decisive defect in the defect size judging circuit 36.

The circuit shown in FIG. 6 is constructed to meet the flow chart shown in FIG. 5 and is capable of coping with a system whose processing capacity is lower than that of the circuit shown in FIG. 4.

Figure 7:
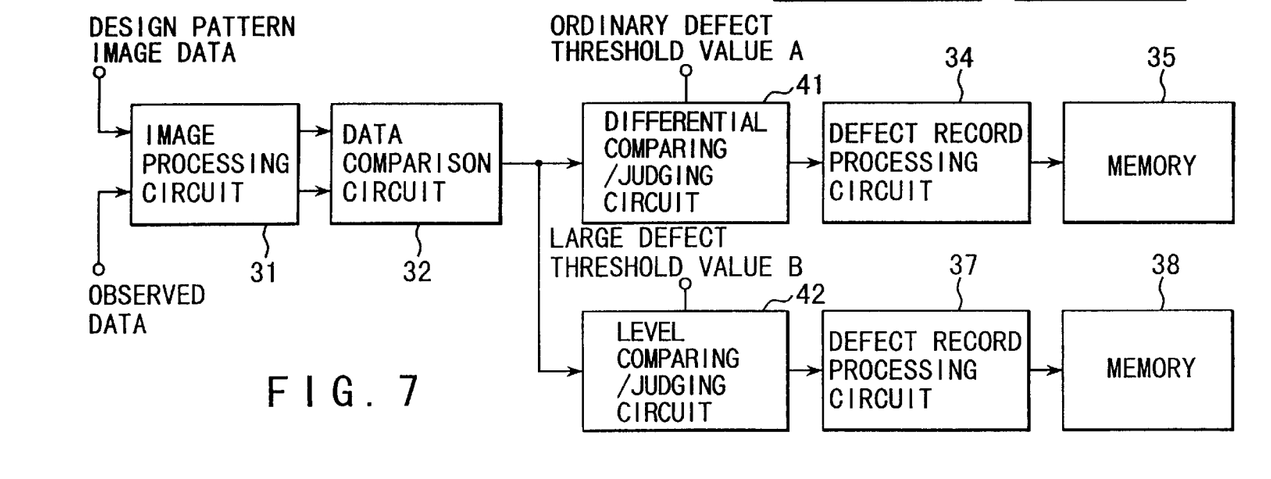
FIG. 7 is a block diagram showing the detailed construction of a comparing/judging circuit according to a third embodiment of the present invention.

FIG. 7 is a block diagram showing in detail the construction of a comparing/judging circuit according to a third embodiment of the present invention. The constituents of the circuit shown in FIG. 7, which are equal to those included in the circuit shown in FIG. 4, are denoted by the same reference numerals so as to omit the detailed description thereof.

In the third embodiment shown in FIG. 7, the defect existence judging circuit 33 and the defect size judging circuit 36, which are shown in FIG. 6, are replaced by a differential comparing/judging circuit 41 and a level comparing/judging circuit 42, respectively. In the third embodiment shown in FIG. 7, the existence of an ordinary defect is judged in the differential comparing/judging circuit 41. On the other hand, the existence of a large defect is judged in the level comparing/judging circuit 42. Let us briefly explain in the following the reason why an ordinary defect and a large defect are judged in the differential comparing/judging circuit 41 and the level comparing/judging circuit 42, respectively, in the third embodiment shown in FIG. 7.

Specifically, in comparing data by performing an image processing, a level comparison is employed in general, in which a difference in, for example, a concentration level between the data items is detected. However, the level comparison method is defective in that the comparison is weak against noise. It follows that it is possible for the noise itself to be detected as a defect if the sensitivity is increased, making it impossible to increase the sensitivity. However, the level comparison method is advantageous in that a defect can be detected over a wide region. On the other hand, rates of change in the signal are compared in the differential comparing method so as to detect a difference between the data items. Since the differential comparing method is strong against noise, compared with the level comparing method, it is possible to increase the sensitivity and, thus, the differential comparing method is adapted for the detection of fine defects. However, the differential comparing method is not adapted for the detection of a defect over a wide range, unlike the level comparing method.

Under the circumstances, it is desirable to use the differential comparing/judging circuit 41 utilizing the differential comparing method for the detection of ordinary defects and the level comparing/judging circuit 42 utilizing the level comparing method for the detection of a large defect, as in the third embodiment shown in FIG. 7.

In any of the first to third embodiments described above, the inspection can be temporarily stopped as shown in FIG. 5 in the case where the existence of a large defect has been judged. To be more specific, in any of these embodiments, it is known to the operator whether the detected defect is sized small enough to be repaired even during the execution of the inspection. Where the detected defect is sized too large to be repaired, the inspection can be temporarily stopped at the detecting stage. In other words, the existence of such a decisive defect can be detected even during the inspection, even if inspection is not applied to the entire region of the sample. As a result, the next sample can be inspected efficiently without spending a useless time. It should also be noted that, where the operator wishes to know the type of the defect, detailed information on the defect can be obtained at an early stage by the visual observation of the operator, if a review treatment is performed after the temporary stopping of the operation. Further, where a plurality of samples are inspected in succession, the next sample can be inspected efficiently without spending a useless time, if the inspection is set in advance to be finished instantly.

As described above, the present invention makes it possible to obtain information at an early stage on, for example, the existence and type of a large defect, where there is a defect which is too large to be repaired. It follows that it is possible to take measures against the defects and to manufacture again the mask at an early stage, leading to a shortened turn-around time as a whole.

It should also be noted that, if the existence of a large defect should be judged, it is possible for the defect to consist of the presence of a removable substance such as dust attached to the sample. In such a case, the sample need not be discarded as a defective article, and the inspection, which has been temporarily stopped, can be continued again by a predetermined instructing means. It follows that the sample need not be disposed of as a defective article, leading to a high yield.

In each of the embodiments described above, the defect existence judging circuit 33 (or the differential comparing/judging circuit 41) and the defect size judging circuit 36 (or the level comparing/judging circuit 42) are used as a defect judging means. In addition, it is possible to use a defect kind judging circuit for judging the kind, such as a white defect or a black defect, of the defect of the pattern on the basis of the result of the comparison performed in the data comparing circuit 32. It should be noted that, if a plurality of threshold values differing from each other depending on the type of the defect are set in advance in the defect size judging circuit 36, it is possible to set an optimum threshold value adapted for the type of the defect.

It should also be noted that employed in each of the embodiments described above is a so-called "die-to-database" comparing system in which the observed data is compared with a design pattern image data prepared on the basis of a design data. However, it is also possible to employ a so-called "die-to-die" comparing system, in which comparison is made between different observed data values of the pattern written within the sample based on the same design data, in a manner similar to that employed in each of the embodiments described above.

Further, the samples to be inspected also include semiconductor wafers, substrates for a liquid crystal display device, etc., in addition to the photomask such as reticle employed in each of the embodiments described above. In the case of applying the inspection to a pattern written on a mask such as reticle, a light transmitted through the sample irradiated with light is used for the inspection as in each of the embodiments described above. However, in the case of applying the inspection to a pattern written on a semiconductor wafer, a light reflected from the sample irradiated with the light is used for the inspection.

Further, the technical idea of the present invention can be embodied in various other fashions within the technical scope of the present invention.

Additional advantages and modifications will readily occur to those skilled in the art. Therefore, the present invention in its broader aspects is not limited to the specific details, representative devices, and illustrated examples shown and described herein. Accordingly, various modifications may be made without departing from the spirit or scope of the general inventive concept as defined by the appended claims and their equivalents.

I claim:

1. A pattern defect inspection apparatus, comprising:
   irradiating means for irradiating a light to a sample having a pattern formed therein;
   beam-condensing means for condensing the transmitted or reflected portion of the light irradiated to said sample by said irradiating means;
   observed data acquiring means for receiving the light condensed by said beam-condensing means so as to acquire the observed data corresponding to the pattern formed in said sample;
   comparing means for comparing a design pattern image data prepared on the basis of a design data corresponding to the pattern formed in said sample with said observed data or for comparing said observed data with another observed data corresponding to a plurality of patterns formed in said sample based on the same design data;

judging means for judging the presence or absence of a defect of a pattern based on the result of comparison made by said comparing means and for also determining whether the size of the defect of the pattern is larger than the predetermined size; and stopping means for temporarily stopping the inspection where the size of the defect detected by said judging means during the inspection is judged to be larger than the predetermined size of a defect, wherein the predetermined sizes of the defects are judged on the basis as to whether the defect can be repaired or not; and wherein said judging means includes means for judging the type of the defect of the pattern based on the result of comparison made by said comparing means and presetting sizes of a plurality of defects according to the types of the defects.

2. The pattern defect inspection apparatus according to claim 1, wherein said judging means includes a first judging means for judging a first defect by differential comparison, and a second judging means for judging a second defect having a size larger than that of said first defect by means of level comparison.

3. The pattern defect inspection apparatus according to claim 1, wherein the predetermined sizes of the defects are judged on the basis as to whether the defect can be repaired or not.

4. The pattern defect inspection apparatus according to claim 1, further comprising observing means for observing the defect detected after the temporary stopping of the inspection performed by said stopping means, and instructing means for instructing an operation which is to be performed in the next step based on the result of the observation performed by said observing means.

5. The pattern defect inspection apparatus according to claim 4, wherein said judging means includes a first judging means for judging a first defect by differential comparison, and a second judging means for judging a second defect having a size larger than that of said first defect by means of level comparison.

6. The pattern defect inspection apparatus according to claim 4, wherein said instructing means gives instruction based on the result of observation made by said observing means as to whether to temporarily stop the inspection or to start up again the inspection.

7. The pattern defect inspection apparatus according to claim 6, wherein said judging means includes a first judging means for judging a first defect by differential comparison, and a second judging means for judging a second defect having a size larger than that of said first defect by means of level comparison.

8. A pattern defect inspection apparatus, comprising:

irradiating means for irradiating a light to a sample having a pattern formed therein;

beam-condensing means for condensing the transmitted or reflected portion of the light irradiated to said sample by said irradiating means;

observed data acquiring means for receiving the light condensed by said beam-condensing means so as to acquire the observed data corresponding to the pattern formed in said sample;

comparing means for comparing a design pattern image data prepared on the basis of a design data corresponding to the pattern formed in said sample with said observed data or for comparing said observed data with another observed data corresponding to a plurality of patterns formed in said sample based on the same design data;

first judging means for judging by a differential comparing method the presence or absence of a first defect of a pattern based on the result of comparison made by said comparing means;

second judging means for judging the presence or absence of a second defect having a size larger than that of said first defect by means of a level comparing method; and stopping means for temporarily stopping the inspection where the said second judging means has judged the presence of a second defect during the inspection.

9. The pattern defect inspection apparatus according to claim 8, further comprising observing means for observing the defect detected after the temporary stopping of the inspection performed by said stopping means, and instructing means for instructing the operation which is to be performed in the next step based on the result of the observation performed by said observing means.

10. The pattern defect inspection apparatus according to claim 9, wherein said instructing means gives instruction based on the result of observation made by said observing means as to whether to temporarily stop the inspection or to start up again the inspection.

11. The pattern defect inspection apparatus according to claim 8, wherein said second judging means includes means for judging the type of the defect of the pattern based on the result of comparison made by said comparing means so as to set a predetermined plurality of sizes of defects coinciding with the kinds of the defects.

12. The pattern defect inspection apparatus according to claim 8, wherein the sizes for judging the presence or absence of said second defect is judged on the basis as to whether the defect can be repaired.

* * * * *